US011079370B2

(12) United States Patent
Kishimoto et al.

(10) Patent No.: US 11,079,370 B2
(45) Date of Patent: Aug. 3, 2021

(54) MEASUREMENT METHOD AND MEASUREMENT DEVICE (71) Applicant: KYOCERA CORPORATION, Kyoto (JP)

(72) Inventors: Kyosuke Kishimoto, Ikoma (JP); Hideharu Kurioka, Osaka (JP); Atsuomi Fukuura, Kyoto (JP)

(73) Assignee: KYOCERA CORPORATION, Kyoto (JP)

( * ) Notice: Subject to any disclaimer, the term of this patent is extended or adjusted under 35 U.S.C. 154(b) by 551 days.

(21) Appl. No.: 15/747,140

(22) PCT Filed: May 31, 2016

(86) PCT No.: PCT/JP2016/066084
§ 371 (c)(1),
(2) Date: Jan. 23, 2018

(87) PCT Pub. No.: WO2017/018049
PCT Pub. Date: Feb. 2, 2017

(65) Prior Publication Data
US 2018/0217132 A1 Aug. 2, 2018

(30) Foreign Application Priority Data
Jul. 30, 2015 (JP) .............................. JP2015-150978

(51) Int. Cl.
G01N 33/53 (2006.01)
G01N 33/566 (2006.01)
G01N 33/543 (2006.01)
G01N 33/72 (2006.01)
G01N 29/44 (2006.01)
G01N 27/414 (2006.01)
G01N 29/02 (2006.01)
G01N 33/68 (2006.01)
G01N 21/552 (2014.01)

(52) U.S. Cl.
CPC ..... *G01N 33/5308* (2013.01); *G01N 27/4145* (2013.01); *G01N 29/022* (2013.01); *G01N 29/4427* (2013.01); *G01N 33/53* (2013.01); *G01N 33/543* (2013.01); *G01N 33/5438* (2013.01); *G01N 33/54386* (2013.01); *G01N 33/566* (2013.01); *G01N 33/6893* (2013.01); *G01N 33/723* (2013.01); *G01N 21/553* (2013.01); *G01N 2291/012* (2013.01); *G01N 2291/02466* (2013.01); *G01N 2291/02809* (2013.01); *G01N 2333/4713* (2013.01); *G01N 2440/38* (2013.01); *G01N 2800/042* (2013.01)

(58) Field of Classification Search
CPC .. G01N 21/553; G01N 29/4427; G01N 33/53; G01N 33/723; G01N 33/5308
USPC ... 435/6.1, 91.1, 91.31, 455, 458, 69.6, 328; 514/44 A; 536/23.1, 25.53; 424/136.1; 530/387.3
See application file for complete search history.

(56) References Cited

U.S. PATENT DOCUMENTS

| 5,206,144 A | 4/1993 | Zeuthen et al. |
| 2011/0311989 A1 | 12/2011 | Miyazaki et al. |
| 2014/0335630 A1 | 11/2014 | Cameron et al. |
| 2015/0024957 A1 | 1/2015 | Cameron et al. |
| 2015/0268239 A1 | 9/2015 | Aizawa et al. |
| 2016/0009794 A1 | 1/2016 | Miyazaki et al. |
| 2016/0299135 A1 | 10/2016 | Cameron et al. |
| 2016/0311895 A1 | 10/2016 | Miyazaki et al. |

FOREIGN PATENT DOCUMENTS

| JP | 07-020437 B | | 3/1995 |
| JP | 2005-130855 A | | 5/2005 |
| JP | 2005 130855 | * | 6/2005 |
| JP | 2005-140553 A | | 6/2005 |
| JP | 5579343 B1 | | 7/2014 |
| JP | 2015-507199 A | | 3/2015 |
| WO | 2010/067611 A1 | | 6/2010 |
| WO | 2015/089575 A1 | | 6/2015 |

OTHER PUBLICATIONS

Michimiro, N., Abstract Publication No. 2005-140553 (Feb. 6, 2005).*
International Search Report dated Aug. 30, 2016, in corresponding International Application No. PCT/JP2016/066084.

* cited by examiner

*Primary Examiner* — Jane J Zara
(74) *Attorney, Agent, or Firm* — Duane Morris LLP (57) ABSTRACT A measurement method includes a measurement step of measuring a first single value and a second signal value, the first signal value being based on a reaction between a first reacting substance and the sample, the second signal value being based on a reaction between a second reacting substance and the sample, the first reacting substance having a higher reactivity to a second detection target than to a first detection target, the second reacting substance having a higher reactivity to the first detection target than to the second detection target.

8 Claims, 6 Drawing Sheets
Specification includes a Sequence Listing.

MEASUREMENT METHOD AND MEASUREMENT DEVICE

TECHNICAL FIELD

The present invention relates to a method and an device for measuring a relationship between a first detection target and a second detection target which are contained in a sample.

BACKGROUND ART

Some substance contained in a sample varies in its concentration in accordance with conditions existing to which the sample is subjected. For example, glycated hemoglobin (HbA1) in the blood, in particular, HbA1c is known as a substance whose level in the blood increases in the body of a diabetic patient, and the level of HbA1c in the blood is thus used as one of diagnostic criteria for diabetes mellitus.

There are heretofore known methods of measuring the concentration of a substance contained in a sample by ELISA technique utilizing antibody. Examples of such a method include a HbA1c content measurement method (for example, refer to Patent Literatures 1 and 2) and a method of measuring HbA1c concentration in the blood by a biosensor equipped with a detecting element bound at its surface with an aptamer (for example, refer to Patent Literature 3).

CITATION LIST

Patent Literature

Patent Literature 1: WO 2010/067611
Patent Literature 2: Japanese Examined Patent Publication JP-B2 07-020437 (1995)
Patent Literature 3: Japanese Unexamined Patent Publication JP-A 2015-507199

SUMMARY OF INVENTION

Technical Problem

However, as a problem involved in the above-described related art, a substance contained in a sample cannot be detected with a high sensitivity without taking much operation time and high cost. As another problem involved in the above-described related art, due to lack of the capability of measuring the concentration of a substance contained in an unrefined sample such as a whole blood sample, sample refining operation needs to be done prior to the measurement of substance concentration.

This has created a demand for a measurement method and a measurement device that enable highly accurate measurement of a detection target substance contained in a sample at lower cost and with simple operation.

Solution to Problem

A measurement method in accordance with an embodiment of the invention comprises: a preparation step of preparing a first reacting substance and a second reacting substance which are located on a surface of a detecting member, the first reacting substance having a higher reactivity to a second detection target than to a first detection target, the second reacting substance having a higher reactivity to the first detection target than to the second detection target; a supply step of supplying a sample containing the first detection target and the second detection target to the surface of the detecting member; a measurement step of, after the supply step, measuring a first signal value based on a reaction between the first reacting substance and the sample, and a second signal value based on a reaction between the second reacting substance and the sample; and a calculation step of calculating a relationship between the first detection target and the second detection target in the sample based on the first signal value and the second signal value.

A measurement device in accordance with an embodiment of the invention comprises: a supply section which supplies a sample containing a first detection target and a second detection target to a first reacting substance and a second reacting substance which are located on a surface of a detecting member, the first reacting substance having a higher reactivity to the second detection target than to the first detection target, the second reacting substance having a higher reactivity to the first detection target than to the second detection target; a measurement section which measures a first signal value based on a reaction between the first reacting substance and the sample, and a second signal value based on a reaction between the second reacting substance and the sample; and a calculation section which calculates a relationship between the first detection target and the second detection target in the sample based on the first signal value and the second signal value.

Advantageous Effects of Invention

The measurement method and the measurement device in accordance with the embodiment of the invention achieve measurement of the relationship between the first detection target and the second detection target contained in the sample with greater accuracy, by easier operation, and at lower cost than does the conventional art. For example, the ratio of HbA1c to total Hb which is one of diagnostic criteria for diabetes mellitus, the ratio of glycoalbumin to albumin which is one of indices for blood sugar control, and the ratio of hemoglobin F to hemoglobin which is used for hereditary hemoglobinopathy (inherited abnormality of Hb) screening can be measured by easier operation, at lower cost, and with greater accuracy than would be the case with the conventional art.

DESCRIPTION OF EMBODIMENTS

<Measurement Method>
(First Embodiment)

A measurement method in accordance with the first embodiment of the invention comprises: a preparation step of preparing a first reacting substance and a second reacting substance which are located on the surface of a detecting member, the first reacting substance having a higher reactivity to a second detection target than to a first detection target, the second reacting substance having a higher reactivity to the first detection target than to the second detection target; a supply step of supplying a sample containing the first detection target and the second detection target to the surface of the detecting member; a measurement step of, after the supply step, measuring a first signal value based on a reaction between the first reacting substance and the sample and a second signal value based on a reaction between the second reacting substance and the sample; and a calculation step of calculating a relationship between the first detection target and the second detection target in the sample based on the first signal value and the second signal value.

The following describes procedural steps in the measurement method according to the present embodiment in order.

The preparation step in this embodiment is intended to prepare the first reacting substance and the second reacting substance which are located on the surface of the detecting member, the first reacting substance having a higher reactivity to the second detection target than to the first detection target, the second reacting substance having a higher reactivity to the first detection target than to the second detection target.

As employed in this description, "the detecting member" refers to, for example, a member provided at its surface with a detecting element which outputs a signal value, such as but not limited to, a surface acoustic wave element, a QCM (Quartz Crystal Microbalance), a SPR (Surface Plasmon Resonance) sensor, or a FET (Field Effect Transistor).

As employed in this description, "the first detection target" refers to a substance contained in the sample, which may be, but is not limited to, a proteinaceous substance, or preferably a disease-associated proteinaceous substance. The proteinaceous substance, which is an organic compound containing amino acid, may be, but is not limited to, protein, polypeptide, peptide, or their modified products such as glycated products. The disease-associated proteinaceous substance, which is a proteinaceous substance that could be associated with a disease, may be, but is not limited to, hemoglobin F (HbF), HbA1c, or glycoalbumin, for example.

As employed in this description, "the second detection target" refers to a substance contained in the sample, which may be, but is not limited to, a proteinaceous substance, or preferably a disease-associated proteinaceous substance. The proteinaceous substance, which is an organic compound containing amino acid, may be, but is not limited to, protein, polypeptide, peptide, or their modified products such as glycated products. The disease-associated proteinaceous substance, which is a proteinaceous substance which could be associated with a disease, may be, but is not limited to, hemoglobin (Hb), HbA0, or albumin, for example. Moreover, when variants are present in the second detection target, the second detection target may be defined as the sum total of all the variants of the second detection target.

Selections of the first detection target and the second detection target may be made according to purposes. For example, for the purpose of diagnosis of diabetes, the first detection target is HbA1c, and the second detection target is HbA0. For example, for the purpose of acquisition of indices for blood sugar control, the first detection target is glycoalbumin, and the second detection target is albumin. For example, for the purpose of hereditary hemoglobinopathy screening, the first detection target is hemoglobin F, and the second detection target is hemoglobin.

As employed in this description, "relationship" refers to a correlation between the first detection target and the second detection target, which may be defined by, but is not limited to, a relation in ratio, a relation in glycation rate, or a relation in mutation rate, for example.

As employed in this description, "reaction" refers to a reaction phenomenon in which the first reacting substance or the second reacting substance exerts an influence upon the sample containing the first detection target and the second detection target with consequent changes in the surface condition of the detecting member, which may be, but is not limited to, a binding reaction, an enzymatic reaction, or a reduction reaction, for example.

As employed in this description, "reactivity" refers to the extent to which the first reacting substance or the second reacting substance exerts an influence upon the first detection target or the second detection target, which may be, but is not limited to, affinity, activity, or associativity, for example.

The following describes one embodiment of the invention with respect to the case where the first detection target is HbA1c, and the second detection target is HbA0. It is noted that the following case is given merely as one embodiment of the invention, and the scope of the invention is not limited to the embodiment as set forth hereunder.

As to the first signal value derived from the first reacting substance having a higher affinity for HbA1c than for HbA0, with the ratio of HbA1c to total Hb in the sample set at a fixed value, when laying off the logarithms of the total Hb concentration as abscissas, under low total Hb concentration conditions, the signal value increases slowly, but, upon the total Hb concentration rising to above a predetermined level, the signal value increases abruptly. Note that the abscissas in linear form indicate that the signal level tends to increase sharply and then converge moderately under lower total Hb concentration conditions. On the other hand, as to the second signal value derived from the second reacting substance having a higher affinity for HbA0 than for HbA1c, with the ratio of HbA1c to total Hb in the sample set at a fixed value, when laying off the logarithms of the total Hb concentration as abscissas, the second signal value increases from the point of time when the total Hb concentration is lower than the first signal value, but is saturated to plateau at the total Hb concentration lower than the first signal value.

Thus, with the ratio of HbA1c to total Hb in the sample set at a fixed value, the first signal value and the second signal value vary differently from each other with an increase in the total Hb concentration in the sample. In the graphical representation of the relationship between the first signal value and the second signal value based on the total Hb concentration and the ratio of HbA1c to the total Hb, the ratio of HbA1c to the total Hb concentration and the first and the second signals show a certain relationship, and, on the basis of this relationship, a calibration curve can be prepared.

It is also possible to calculate the ratio of HbA1c to the total Hb in the sample based on the calibration curve prepared in advance through concurrent measurements of the first signal value derived from the first reacting substance and the second signal value derived from the second reacting substance. That is, the measurement method according to the present embodiment enables calculation of the ratio of HbA1c to total Hb in the sample with simple operation.

By way of one embodiment, the first reacting substance has an affinity for HbA1c which is about 5 to 30 times higher than for HbA0, and, the second reacting substance has an affinity for HbA0 which is 100 or more times higher than for HbA1c. Any one of the first reacting substance and the second reacting substance may have affinity for both of HbA0 and HbA1c. For example, the first reacting substance may have different affinities for HbA0 and HbA1c as described above, whereas the second reacting substance may have affinity for HbA0 alone. Note that the first reacting substance may have affinity for one of HbA0 and HbA1c, whereas the second reacting substance may have affinity for the other.

As employed in this description, each of "the first reacting substance" and "the second reacting substance" may be selected from the group consisting of protein, polypeptide, peptide, nucleic acid, and boronic acid compound, for example. For example, the first reacting substance and the second reacting substance may be ligands including an antibody, an aptamer, peptide, etc. For example, the antibody may be a polyclonal antibody or a monoclonal antibody, and, the aptamer may be an RNA aptamer or a DNA aptamer, for example. The first reacting substance and the second reacting substance may either be identical with or different from each other. For example, each of the first reacting substance and the second reacting substance is an aptamer, or, one of them is an antibody and the other is an aptamer. Moreover, where the first detection target, as well as the second detection target, is a glycated substance such as HbA1c, then the first reacting substance, as well as the second reacting substance, may be a boronic acid compound.

The supply step in this embodiment is intended to supply a sample containing HbA0 and HbA1c to the surface of the detecting member. In this step, the first reacting substance immobilized on the surface of the detecting member undergoes reactions with HbA0 and/or HbA1c, and the second reacting substance immobilized on the surface of the detecting member undergoes reactions with HbA0 and/or HbA1c. Examples of how to immobilize the substance at the surface of the detecting member include immobilizing the substance on the surface through chemical binding or covalent binding, and adhering the substance to the surface simply by physical force.

The measurement step in this embodiment is intended to measure the first signal value based on the reaction between the first reacting substance and the sample and the second signal value based on the reaction between the second reacting substance and the sample after the supply step.

In this embodiment, the detecting member comprises a surface acoustic wave element, and, in this case, phase characteristic values of the surface acoustic wave element may be used as the first signal value based on the reaction between the first reacting substance and the sample and the second signal value based on the reaction between the second reacting substance and the sample.

The calculation step in this embodiment is intended to calculate the ratio of HbA1c to total Hb in the sample based on the first signal value and the second signal value.

The calculation step in this embodiment may be intended to calculate the HbA1c-to-total Hb ratio based on a calibration curve which is prepared in advance, the first and second signal values.

As employed in this description, "calibration curve" refer to data required to calculate the above-described desired relationship. For example, in the case of calculating the ratio of HbA1c to total Hb, the calibration curve may be prepared based on a first reference signal value and a second reference signal value, the first reference signal value and the second reference signal values being measured with use of a plurality of reference samples, each of the plurality of reference samples being preliminarily assigned with total Hb concentration and HbA1c-to-total Hb ratio, the first reference signal value being based on a reaction between the first reacting substance and each of the reference samples, the second reference signal value being based on a reaction between the second reacting substance and each of the reference samples.

As employed in this description, "sample" refers to, for example, a blood sample such as a whole blood sample, or a blood sample diluted with, for example, a buffer solution. The sample may be one other than a blood sample.

As a modified example, a cleaning step of delivering a cleaning solution to the surface of the detecting member may be carried out between the supply step and the measurement step. The addition of the cleaning step permits removal of foreign matter composed of substances excluded from the total Hb contained in the sample from the surface of the detecting member, thus eliminating the influence of foreign matter on the operation steps subsequent to the cleaning step, whereby the first signal value and the second signal value can be measured in the measurement step with greater accuracy.

As employed in this description, "cleaning solution" refers to, for example, a buffer solution. While examples of the buffer solution include, but are not limited to, a phosphate buffer solution, and may thus be any suitable one of heretofore known buffer solutions.

The following describes one example of the first embodiment with respect to the case where the detecting member comprises a surface acoustic wave element; a first RNA aptamer having a higher affinity for HbA1c than for HbA0 is used as the first reacting substance; a second RNA aptamer having a higher affinity for HbA0 than for HbA1c is used as the second reacting substance; and a blood sample is used as the sample.

That is, one example of the first embodiment may be designed as a measurement method comprising: a preparation step of preparing a first RNA aptamer and a second RNA aptamer immobilized on the surface of a detecting member, the first RNA aptamer having a higher affinity for HbA1c than for HbA0, the second RNA aptamer having a higher affinity for HbA0 than for HbA1c; a supply step of supplying a blood sample containing HbA0 and HbA1c to the surface of the detecting member; a measurement step of, after the supply step, measuring a first signal value based on a binding of the first RNA aptamer with HbA0 and HbA1c, and a second signal value based on a binding of the second RNA aptamer with HbA0 and HbA1c; and a calculation step of calculating the ratio of HbA1c to total Hb in the blood sample based on the first signal value and the second signal value.

<Measurement Device>
(Second Embodiment)

Figure 1:
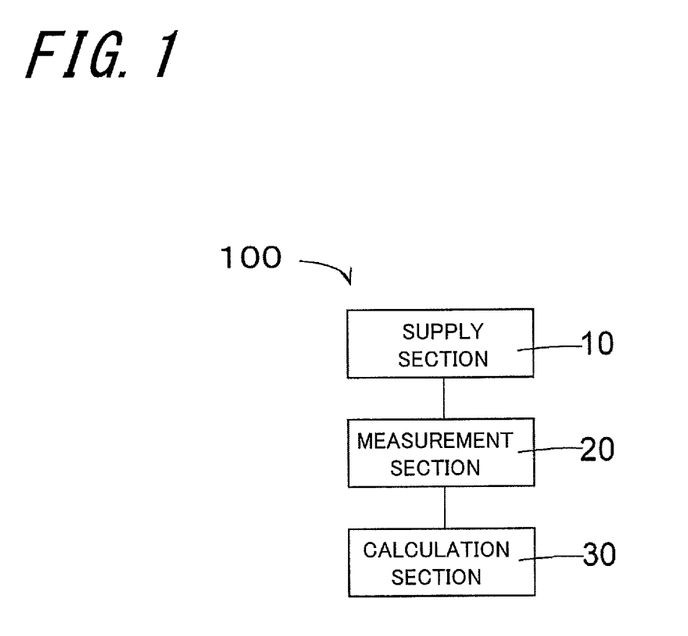
FIG. 1 is a diagram showing the structure of a measurement device 100 in accordance with an embodiment of the invention.

FIG. 1 is a block diagram showing the functional structure of a measurement device 100 in accordance with a second embodiment of the invention. The measurement method in accordance with the first embodiment of the invention is executed by the measurement device 100.

The following describes one embodiment of the invention with respect to the case where the first detection target is HbA1c, and the second detection target is HbA0. It is noted that the following case is given merely as one embodiment of the invention, and the scope of the invention is not limited to the embodiment as set forth hereunder.

The measurement device 100 comprises: a supply section which supplies a sample containing HbA0 and HbA1c to a first reacting substance and a second reacting substance immobilized on a surface of a detecting member, the first reacting substance having a higher affinity for HbA1c than for HbA0, the second reacting substance having a higher affinity for HbA0 than for HbA1c; a measurement section which measures a first signal value based on a reaction between the first reacting substance and the sample, and a second signal value based on a reaction between the second reacting substance and the sample; and a calculation section which calculates the ratio of HbA1c to total Hb in the sample based on the first signal value and the second signal value.

The supply section 10 includes, but is not limited to, a detecting member bearing immobilized first and second reacting substances; a supply path for the supply of a sample to the detecting member; and a pump for allowing the sample to flow into the supply path.

The measurement section 20 may be composed of, but is not limited to, a device comprising an element which inputs a signal to the detecting member and acquires a predetermined signal value based on signal output produced from the detecting member.

The calculation section 30 may be composed of, but is not limited to, an arithmetic unit comprising an arithmetic element which determines the ratio of HbA1c to total Hb based on the first signal value and the second signal value measured by the measurement section 20.

The following describes an example of a biosensor device used for the measurement device 100. The biosensor device constitutes the supply section, the measurement section, and the calculation section.

Figure 2:
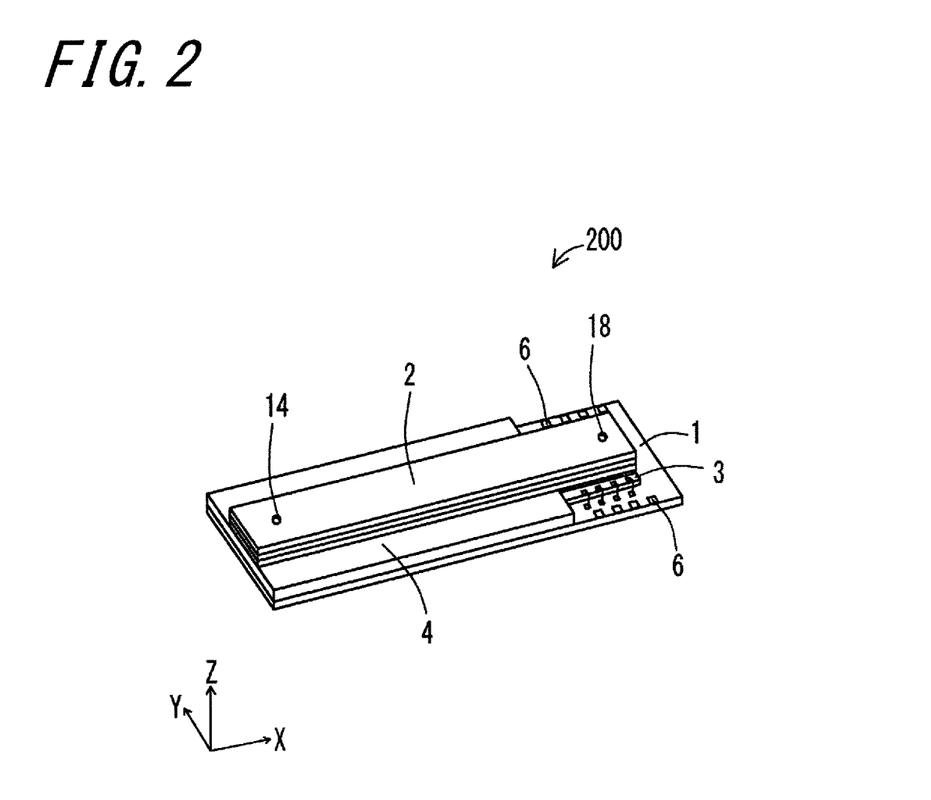
FIG. 2 is a perspective view of a biosensor device 200 in accordance with the embodiment of the invention.
Figure 3:
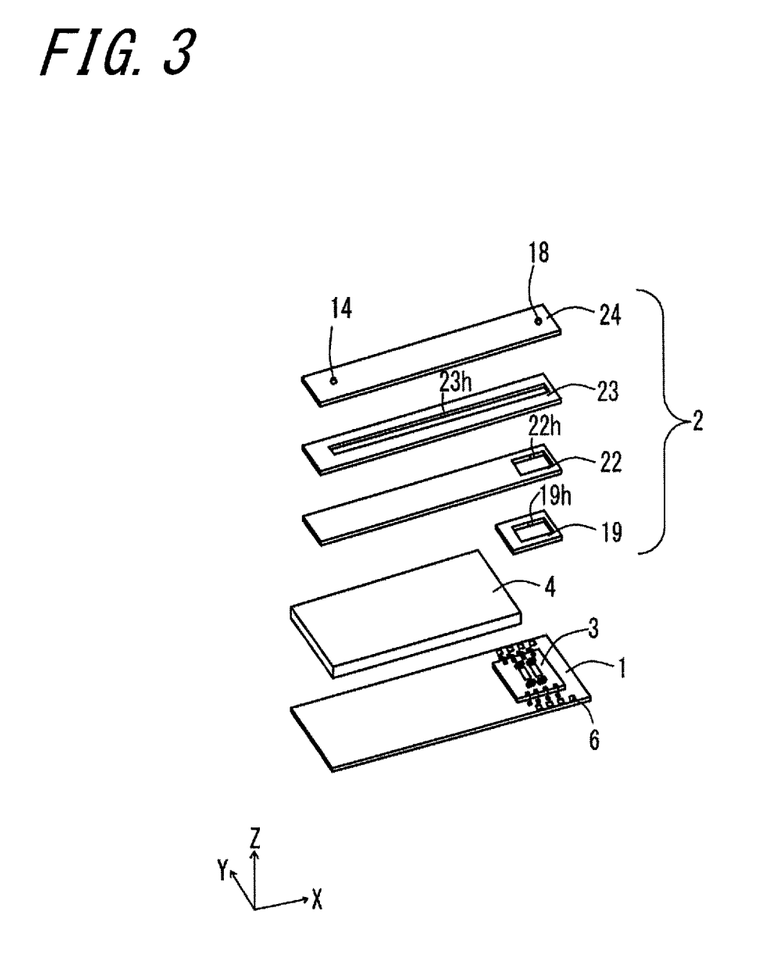
FIG. 3 is an exploded perspective view of a biosensor device 200 in accordance with the embodiment of the invention.
Figure 4:
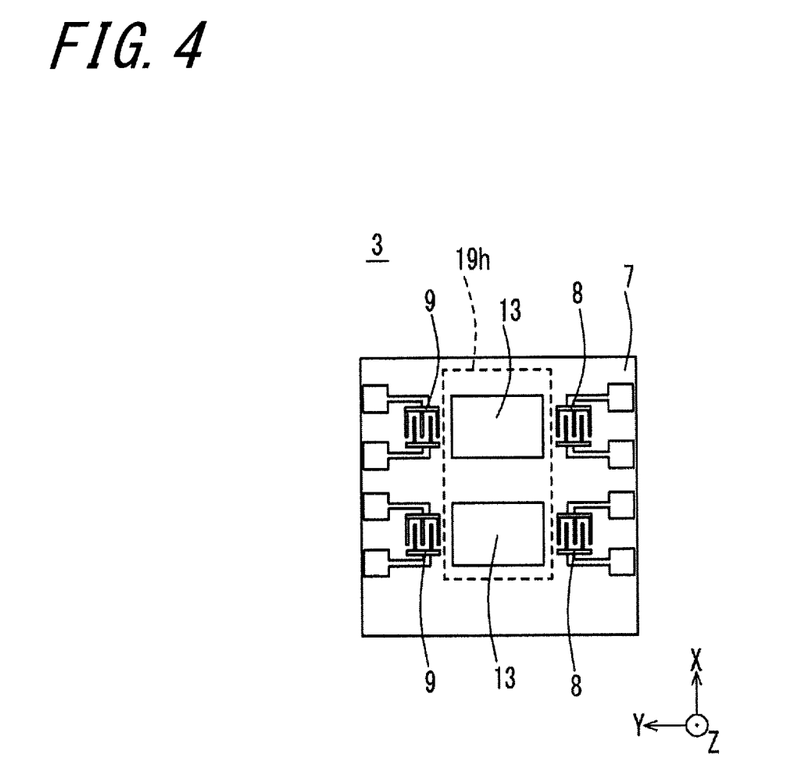
FIG. 4 is a plan view of a detecting element 3 in accordance with the embodiment of the invention.

FIGS. 2 and 3 are a perspective view and an exploded perspective view, respectively, of the biosensor device 200, and, FIG. 4 is a plan view of a detecting element 3.

The biosensor device 200 is composed of a substrate 1, a flow channel structure 2, and a detecting element 3. As shown in FIG. 2, the flow channel structure 2 is disposed on the substrate 1, with the detecting element 3 and a support member 4 lying between them. The flow channel structure 2 has an inlet port 14 as an entry of a liquid sample on one longitudinal end side, and a flow channel which is in communication with the inlet port 14 is formed therein. The substrate 1 has a flat plate shape, is, for example, a resin substrate, a ceramic substrate or the like, and is provided with a wiring conductor or the like on a surface layer or inner layer.

The detecting element 3 is mounted on one end side of an upper surface of the substrate 1. Terminals 6 electrically connected to the detecting element 3 are provided on both sides of the detecting element 3. the device, the arithmetic unit, and the like are connected to the terminals 6.

The detecting element 3 is a surface acoustic wave element and includes a piezoelectric substrate 7, a first IDT (Inter Digital Transducer) electrode 8, a second IDT electrode 9, and a detecting section 13. The piezoelectric substrate 7 is composed of a substrate of single crystal having piezoelectric properties, such as lithium tantalate. The first IDT electrode 8 comprises a pair of comb electrodes. Each comb electrode includes two bus bars opposed to each other, and a plurality of electrode fingers each extending from corresponding one of the bus bars toward the other. The pair of comb electrodes is disposed so that the plurality of electrode fingers are arranged in an interdigitated pattern. The second IDT electrode 9 is structurally similar to the first IDT electrode 8. The first IDT electrode 8 and the second IDT electrode 9 constitute a transversal IDT electrode.

The first IDT electrode 8 serves to generate a predetermined surface acoustic wave, and the second IDT electrode 9 serves to receive the surface acoustic wave generated by the first IDT electrode 8. The first IDT electrode 8 and the second IDT electrode 9 are each formed of, for example, aluminum or an alloy of aluminum and copper.

The detecting section 13 is disposed between the first IDT electrode 8 and the second IDT electrode 9. The detecting section 13 has a two-layer structure consisting of chromium and a film of gold formed on the chromium. On the surface of the metallic film of the detecting section 13 is immobilized the first reacting substance or the second reacting substance which reacts with HbA0 and HbA1c. Upon the supply of a sample to the detecting section, HbA0 and HbA1c contained in the sample undergo reactions with the first reacting substance or the second reacting substance.

Given that the first IDT electrode 8, the second IDT electrode 9, and the detecting section 13 are grouped into a set, the detecting element 3 is provided with two such sets. In this case, for example, the detecting section 13 of one of the sets can measure the sample, whereas the detecting section 13 of the other can measure a reference value. For example, in the detecting section 13 of the other set, the first reacting substance and the second reacting substance do not react.

In such a detecting element 3 utilizing surface acoustic waves, to begin with, an external signal with a predetermined voltage is applied to the first IDT electrode 8. Then, in the range of the first IDT electrode 8, the surface of the piezoelectric substrate 7 is excited, thus producing a surface acoustic wave having a predetermined frequency. Part of the thereby produced surface acoustic wave propagates toward the detecting section 13, passes through the detecting section 13, and is received by the second IDT electrode 9. In the detecting section 13, the first reacting substance or the second reacting substance undergoes reactions in accordance with the amounts of HbA0 and HbA1c, with the consequence that the mass of the detecting section 13 is increased correspondingly. As the phase of the surface acoustic wave passing through the detecting section 13 changes with the increase in mass, a voltage corresponding to the change is developed in the second IDT electrode 9. The difference in phase between the signal applied to the first IDT electrode 8 and the signal outputted from the second IDT electrode 9 is measured as a phase change.

Furthermore, the support member 4 is mounted on the upper surface of the substrate 1 to support the flow channel structure 2. The flow channel structure 2 is placed so as to cover at least part of the detecting element 3. For example, the flow channel structure 2 is composed of a first adherent layer 19, a first hydrophilic sheet 22, a second adherent layer 23, and a second hydrophilic sheet 24.

The first adherent layer 19 has a frame shape having a through hole 19h from which part of the detecting element 3 is exposed. The first hydrophilic sheet 22 is laminated on the first adherent layer 19. The first hydrophilic sheet 22 has a through hole 22h which is similar to the through hole 19h, and, the first adherent layer 19 and the first hydrophilic sheet 22 are stacked together so that their through holes are brought into communication with each other. The second adherent layer 23 is laminated on the first hydrophilic sheet 22. The second adherent layer 23 has a longitudinally extending through hole 23h constituting a flow channel. One end of the through hole 23h extends to a position overlapping with the through hole 22h. The second hydrophilic sheet 24 is laminated on the second adherent layer 23. The second hydrophilic sheet 24 is provided with an inlet port 14 and an outlet port 18, each of which is defined by a through hole, located closer to opposite end sides thereof, respectively. The inlet port 14 and the outlet port 18 are provided in positions overlapping with the through hole 23h.

EXAMPLES

The following describes examples of the measurement method according to the above-described embodiment.

Example 1: Calibration Curve Preparation

Biacore T200 (manufactured by GE Healthcare) which was a molecular interaction analyzer was used. The analyzer has four flow cells (Fc1 to Fc4).

Series S Sensor Chip SA (manufactured by GE Healthcare) was used as the substrate (base body).

The following describes a procedure to immobilize an RNA aptamer A (SEQ ID No. 1) serving as the first reacting substance and an RNA aptamer B (SEQ ID No. 2) serving as the second reacting substance on the Series S Sensor Chip SA and measure phase characteristic values (hereafter also referred to as signal values) based on a binding of the RNA aptamer A with HbA0 and HbA1c, as well as a binding of the RNA aptamer B with HbA0 and HbA1c.

As each the RNA aptamer A and the RNA aptamer B, there was used an annealed aptamer (3-minute retention after heating to 85° C., cool-down to 25° C. at the rate of −0.1° C./sec) with adenine and uracil substituted at the 2′ position for a fluorine group. The RNA aptamer A and the RNA aptamer B are externally synthesized aptamers.

A dissociation constant $K_D$ of the RNA aptamer A with respect to HbA0 was 160 nM. The RNA aptamer A was not bound to HbA1c at all, or, if any, the extent of binding was extremely low. That is, the RNA aptamer A has a higher affinity for HbA0 than for HbA1c.

A dissociation constant $K_D$ of the RNA aptamer B with respect to HbA0 was 1000 nM, and a dissociation constant $K_D$ of the RNA aptamer B with respect to HbA1c was 50 nM. That is, the RNA aptamer B has a higher affinity for HbA1c than for HbA0.

As a running buffer solution, there was used a solution of HBS-P (manufactured by GE Healthcare) with $MgCl_2$ added so as to be adjusted to a 1 mM level (0.01 M HEPES (pH 7.4), 0.15 M NaCl, 0.005% Surfactant P20, 1 mM $MgCl_2$), which will hereafter be referred to as HBS-P (+$MgCl_2$).

Moreover, for the purpose of preparing a calibration curve, as a reference sample, there was used a solution obtained by denaturing a certified reference material for measurement of HbA1c (JCCRM 423-9b in freeze-dried form) manufactured by Reference Material Institute for Clinical Chemistry Standards, removing a surfactant by a column after bringing the denaturation to a stop, and thereafter substituting HBS-P (+$MgCl_2$) for the solvent by a desalting column.

In Step (1), each and every flow cell (Fc1 to Fc4) was washed with 10 mM NaOH for 1 minute at a flow rate of 20 μl/min.

In Step (2), the operation in Step (1) was repeated four times.

In Step (3), 5 μM TTTTTTTTTTTTTTTTTT (SEQ ID No. 3) having biotin at the 5′-terminal was allowed to flow to the flow cells Fc1 to Fc4 for 6 minutes at a flow rate of 5 μl/min for immobilization. At this time, dilution was effected with use of a HBS-P (+$MgCl_2$) solution.

In Step (4), the flow cells Fc1 to Fc4 were washed with 10 mM NaOH for 1 minute at a flow rate of 20 μl/min.

In Step (5), the operation in Step (4) was repeated four times.

In Step (6), 0.5 μM RNA aptamer A was allowed to flow to the flow cell Fc2 for 2 minutes at a flow rate of 5 μl/min for immobilization, followed by 1 minute monitoring of dissociation.

In Step (7), a reference sample having a total Hb concentration of 0.01 μM and a HbA1c-to-total Hb ratio of 5.56% was allowed to flow to the flow cell Fc1 and the flow cell Fc2 successively in the order named for 5 minutes at a flow rate of 20 μl/min, followed by 2 minute monitoring of dissociation. The flow cell Fc1 was used to obtain a reference value with respect to the flow cell Fc2.

In Step (8), the flow cells Fc1 and Fc2 were washed with 10 mM NaOH for 1 minute at a flow rate of 20 μl/min. With this operation, the RNA aptamer A is dissociated, whereupon the Series S Sensor Chip SA is again in Step (5)-completed condition.

After that, in Step (9), the operations in Steps (6) through (8) were performed for reference samples having total Hb concentrations of 0.05 μM, 0.1 μM, 0.5 μM, 1 μM, 2 μM, 5 μM, and 10 μM, respectively. The ratio of HbA1c to total Hb in each reference sample was set at 5.56%.

Figure 5A:
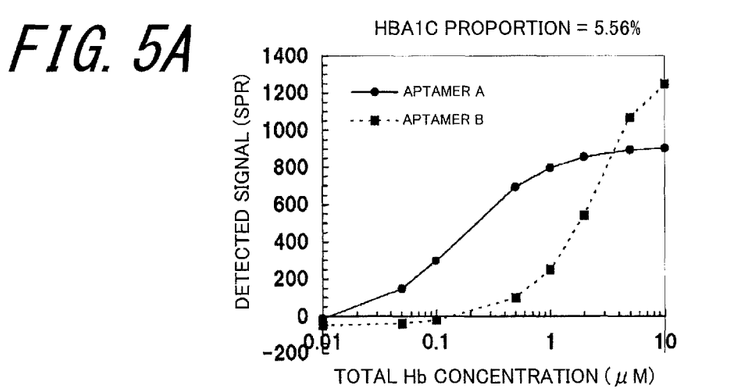
FIGS. 5A to 5C are charts indicating experimental data on a measurement method in accordance with the embodiment of the invention.

After that, in Step (10), the operations in Steps (6) through (9) were performed on the flow cells Fc3 and Fc4 with use of the RNA aptamer B. The RNA aptamer B was immobilized on the flow cell Fc4, and, the flow cell Fc3 was used to obtain a reference value with respect to the flow cell Fc4. Otherwise, the operations are similar to those as described above. The results are shown in FIG. 5A.

Figure 5B:
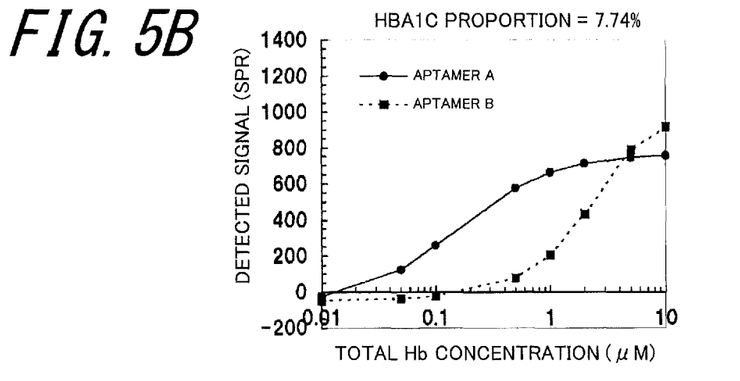

Moreover, the operations in Steps (1) through (10) were performed for reference samples having total Hb concentrations of 0.01 μM, 0.05 μM, 0.1 μM, 0.5 μM, 1 μM, 2 μM, 5 μM, and 10 μM, respectively, each of which was set for a HbA1c-to-total Hb ratio of 7.74%. The results are shown in FIG. 5B.

Figure 5C:
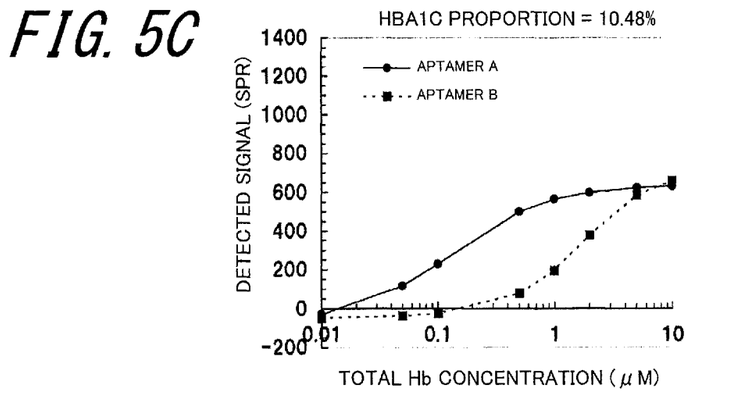

Moreover, the operations in Steps (1) through (10) were performed for reference samples having total Hb concentrations of 0.01 μM, 0.05 μM, 0.1 μM, 0.5 μM, 1 μM, 2 μM, 5 μM, and 10 μM, respectively, each of which was set for a HbA1c-to-total Hb ratio of 10.48%. The results are shown in FIG. 5C.

Figure 6A:
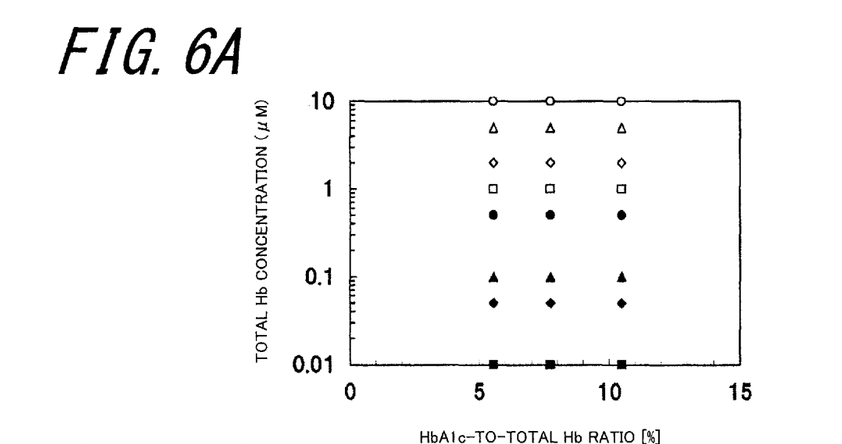
FIGS. 6A and 6B are charts indicating experimental data on the measurement method in accordance with the embodiment of the invention.
Figure 6B:
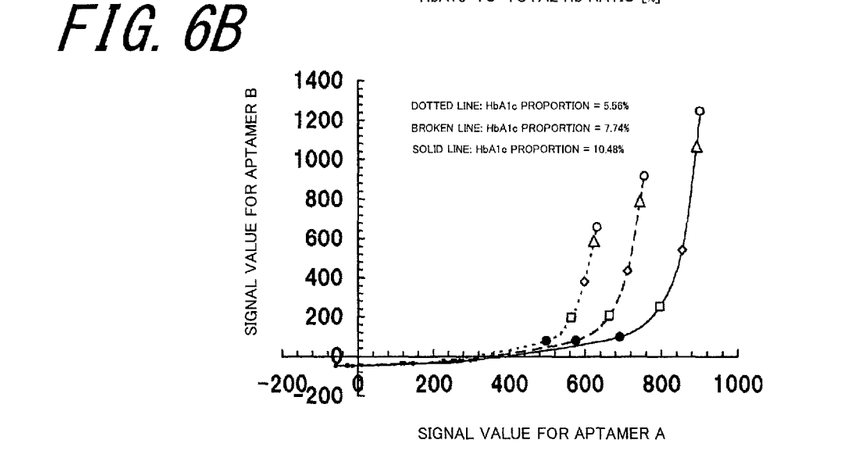

FIG. 6A is a diagram plotting the individual reference samples described with reference to FIGS. 5A to 5C in respect of the relationship between total Hb concentration and HbA1c-to-total Hb ratio. In FIG. 6B, the ordinate axis represents RNA aptamer B-related signal values for the individual plots indicated in FIG. 6A, and the abscissa axis represents RNA aptamer A-related signal values for the individual plots indicated in FIG. 6A. More specifically, a curve indicated by the dotted line has been obtained by connecting the results of measurements on the reference samples having a HbA1c-to-total Hb ratio of 5.56% to one another; a curve indicated by the broken line has been obtained by connecting the results of measurements on the reference samples having a HbA1c-to-total Hb ratio of 7.74% to one another; and a curve indicated by the solid line has been obtained by connecting the results of measurements on the reference samples having a HbA1c-to-total Hb ratio of 10.48% to one another.

The hollow circular mark, the hollow triangular mark, the hollow rhombic mark, and the hollow square mark shown in FIG. 6A correspond to the hollow circular mark, the hollow triangular mark, the hollow rhombic mark, and the hollow square mark shown in FIG. 6B, respectively.

Thus, as shown in FIG. 6B, the calibration curve was prepared for the reference samples in a range of from 1 to 10 µM in total Hb concentration, and from 5.56 to 10.48% in HbA1c-to-total Hb ratio.

Example 2: Blood Sample Measurement

With the reference sample replaced with a blood sample, the operations in Steps (1) through (7) in Example 1 were performed to obtain signal values for the aptamer A and the aptamer B. On the basis of the signal values thus obtained and the calibration curve prepared in Example 1, the ratio of HbA1c to total Hb in the blood sample was calculated.

More specifically, calculation of the ratio of HbA1c to total Hb in the blood sample was effected based on the data obtained by plotting the signal values for the aptamer A and the aptamer B in calibration curve form as shown in FIG. 6B, and thereafter projecting the calibration curve on a plane as shown in FIG. 6A. Moreover, the concentration of total Hb contained in the blood sample could be calculated with use of the plots shown in FIG. 6A.

Example 3: Example Using RNA Aptamers C and D

With the exception that an RNA aptamer C (SEQ ID No. 4) was used as the first reacting substance in place of the RNA aptamer A, and an RNA aptamer D (SEQ ID No. 5) was used as the second reacting substance in place of the RNA aptamer B, calibration curve preparation and blood sample measurement were performed in the same manner as adopted in Examples 1 and 2 unless otherwise specified.

In Step (1), each and every flow cell (Fc1 to Fc4) was washed with 10 mM NaOH for 1 minute at a flow rate of 20 µl/min.

In Step (2), the operation in Step (1) was repeated four times in total.

In Step (3), 1 µM RNA aptamer C having biotin at the 5'-terminal and 1 µM RNA aptamer D having biotin at the 5'-terminal were allowed to flow to the flow cell Fc2 and the flow cell Fc4, respectively, for 8 minutes at a flow rate of 5 µl/min for immobilization. At this time, the aptamer was diluted with a HBS-P (+MgCl$_2$) solution.

In Step (4), the flow cells Fc1 to Fc4 were washed with 10 mM NaOH for 1 minute at a flow rate of 20 µl/min.

In Step (5), the operation in Step (4) was repeated four times in total.

In Step (6), a reference sample having a total Hb concentration of 0.01 µM and a HbA1c-to-total Hb ratio of 5.61% was allowed to flow to the flow cell Fc1 and the flow cell Fc2 successively in the order named for 5 minutes at a flow rate of 20 µl/min, followed by 2 minute monitoring of dissociation. The flow cell Fc1 was used to obtain a reference value with respect to the flow cell Fc2.

In Step (7), the flow cells Fc1 and Fc2 have been washed with 10 mM NaOH for 1 minute at a flow rate of 20 µl/min. With this operation, the reference sample is dissociated, whereupon the Series S Sensor Chip SA is again in Step (5)-completed condition.

After that, in Step (8), the operations in Steps (6) and (7) were performed for reference samples having total Hb concentrations of 0.05 µM, 0.1 µM, 0.5 µM, 1 µM, 2 µM, 5 µM, and 10 µM, respectively. The ratio of HbA1c to total Hb in each reference sample was set at 5.61%.

In Step (9), a reference sample having a total Hb concentration of 0.01 µM and a HbA1c-to-total Hb ratio of 5.61% was allowed to flow to the flow cell Fc3 and the flow cell Fc4 successively in the order named for 5 minutes at a flow rate of 20 µl/min, followed by 2 minute monitoring of dissociation. The flow cell Fc3 was used to obtain a reference value with respect to the flow cell Fc4.

In Step (10), the flow cells Fc3 and Fc4 were washed with 10 mM NaOH for 1 minute at a flow rate of 20 µl/min. With this operation, the reference sample is dissociated, whereupon the Series S Sensor Chip SA is again in Step (5)-completed condition.

After that, in Step (11), the operations in Steps (9) and (10) were performed for reference samples having total Hb concentrations of 0.05 µM, 0.1 µM, 0.5 µM, 1 µM, 2 µM, 5 µM, and 10 µM, respectively. The ratio of HbA1c to total Hb in each reference sample was set at 5.61%.

The operations in Steps (6) through (11) were performed for reference samples having total Hb concentrations of 0.01 µM, 0.05 µM, 0.1 µM, 0.5 µM, 1 µM, 2 µM, 5 µM, and 10 µM, respectively, each of which was set for a HbA1c-to-total Hb ratio of 7.71%.

Moreover, the operations in Steps (6) through (11) were performed for reference samples having total Hb concentrations of 0.01 µM, 0.05 µM, 0.1 µM, 0.5 µM, 1 µM, 2 µM, 5 µM, and 10 µM, respectively, each of which was set for a HbA1c-to-total Hb ratio of 10.55%.

There was prepared a calibration curve for the reference samples ranging in total Hb concentration from 1 to 10 µM, and in HbA1c-to-total Hb ratio from 5.61 to 10.55%.

With the reference sample replaced with a blood sample, the operations in Steps (1) through (7) in Example 3 was performed to obtain signal values for the RNA aptamer C and the RNA aptamer D. On the basis of the signal values thus obtained and the calibration curve prepared in Example 3, the ratio of HbA1c to total Hb in the blood sample was calculated. Consequently, the concentration of total Hb contained in the blood sample could be successfully calculated.

Example 4: Example Using Aptamers with Amino Group at the Terminal

The following describes a procedure to immobilize RNA aptamers C and D on a mounting substrate, each of which has an amino group at the 5'-terminal via oligo ethylene glycol (OEG) hexamer, and detect HbA1c.

In Step (1), the detecting element 3 was prepared. Au (gold) was used for an immobilization film 13a.

In Step (2), a region including the detecting section 13 was washed with SH-303 (manufactured by KANTO CHEMICAL CO., INC.).

In the following subsequent operations in Steps (3) through (7), the RNA aptamers C and D were immobilized on the Au-made immobilization film. Note that the detecting element 3 had a plurality of detecting sections 13, and, the RNA aptamer C and the RNA aptamer D were immobilized on the different detecting sections 13.

In Step (3), the detecting element 3 was immersed in ethanol containing Carboxy-EG6-Undecanethiol (manufactured by DOJINDO LABORATORIES) dissolved at a concentration of 250 uM and Hydroxy-EG3-Undecanethiol (manufactured by DOJINDO LABORATORIES) dissolved at a concentration of 750 uM for 16 hours.

In Step (4), the detecting element 3 was rinsed in ethanol and ultrapure water, and then dried with nitrogen.

In Step (5), the detecting element 3 was immersed in a 10 mM NaOH solution having a SDS content of 0.5% for 3 minutes. After repeating the same operation three times in total, the detecting element 3 was rinsed in ultrapure water, and then dried with nitrogen.

In Step (6), a mixture of a 1-Ethyl-3-(3-dimethylaminopropyl) carbodiimide aqueous solution, a N-Hydroxysuccinimide aqueous solution, and hydrochloric acid was dropped on to the region including the detecting section 13, and, the region was allowed to stand for 10 minutes.

In Step (7), after removing the mixture, a mixture having the same composition as described above was dropped on to the region including the detecting section 13, and, the region was allowed to stand for 10 minutes.

In Step (8), the operation in Step (7) was repeated four times.

In Step (9), the carboxyl group at the terminal of Carboxy-EG6-Undecanethiol was active-esterified by washing using a 10 mM sodium acetate aqueous solution having a pH of 5.0.

In Step (10), each of the RNA aptamers C and D having an amino group at the 5'-terminal was dissolved in a NaCl-containing 100 mM HEPES buffer solution having a pH of 7.4 on an individual basis, and, the prepared solutions were dropped on to different regions including the detecting section 13, and, each region was allowed to stand for 30 minutes.

In Step (11), after removing the solutions, the same RNA aptamer solution as described above was dropped on to the corresponding region including the detecting section 13, and, each region was allowed to stand for 30 minutes.

In Step (12), after repeating the operation in Step (11), the regions including the detecting section 13 were washed with a 10 mM sodium acetate aqueous solution having a pH of 5.0 and 1 mM $MgCl_2$-containing HBS-P (manufactured by GE Healthcare) to effect an amide binding of the esterified carboxyl group with the amino group which via OEG exists at the 5'-terminal of each of the RNA aptamers C and D. The operations in Steps (10) and (11) were not carried out in the case of forming a reference electrode.

In Step (13), for the purpose of preparing a calibration curve, as a reference sample, there was used a solution obtained by denaturing a certified reference material for measurement of HbA1c (JCCRM 411-3 manufactured by Reference Material Institute for Clinical Chemistry Standards), bringing the denaturation to a stop after removing a surfactant using a column, and thereafter substituting 1 mM $MgCl_2$-containing HBS-P for the solvent by a desalting column.

In Step (14), a reference sample which was diluted with 1 mM $MgCl_2$-containing HBS-P so as to be adjusted to a 5 nM level (wherein HbA1c constitutes 5.10% of the total sample) was delivered to the detecting element 3 through a flow channel 15, and the amount of phase changes obtained as the result of 30 minute reactions was measured.

In Step (15), the detecting element 3 was washed by delivering 10 mM NaOH to the detecting element 3 through the flow channel 15, followed by standing for 1 minute. With this operation, the reference sample is dissociated from the RNA aptamers C and D, whereupon the detecting element is again in Step (12)-completed condition.

In Step (16), a reference sample which has been diluted with 1 mM $MgCl_2$-containing HBS-P so as to be adjusted to a 5 nM level (wherein HbA1c constitutes 11.98% of the total sample) was delivered to the detecting element 3 through the flow channel 15, and the amount of phase changes obtained as the result of 30 minute reactions was measured.

In Step (17), the detecting element 3 was washed by delivering 10 mM NaOH to the detecting element 3 through the flow channel 15, followed by standing for 1 minute. With this operation, the reference sample is dissociated from the RNA aptamers C and D, whereupon the detecting element is again in Step (12)—completed condition.

In Step (18), the operations in Steps (14) through (17) were performed with use of reference samples adjusted to a 50 nM level, a 500 nM level, a 5 μM level, and a 50 μM level, respectively.

The results showed that the use of highly stable amide binding permitted highly stable immobilization of the RNA aptamers C and D.

The calibration curve was prepared for the reference samples in a range of from 1 to 10 μM in total Hb concentration, and from 5.10 to 11.98% in HbA1c-to-total Hb ratio.

With the reference sample replaced with a blood sample, the operations in Steps (14) through (17) were performed to obtain signal values for the RNA aptamers C and D. On the basis of the signal values thus obtained and the calibration curve prepared in Example 4, the ratio of HbA1c to total Hb in the blood sample was calculated. The concentration of total Hb contained in the blood sample could be successfully calculated.

As a matter of course, the invention is not limited to the embodiments and the modified examples described heretofore, and thus modifications and changes are possible without departing from the scope of the invention.

REFERENCE SIGNS LIST

1: Substrate
2: Flow channel structure
3: Detecting element
4: Support member
6: Terminal
7: Piezoelectric substrate
8: First IDT electrode
9: Second IDT electrode
10: Supply section
13: Detecting section
14: Inlet port
20: Measurement section
30: Calculation section
100: Measurement device
200: Biosensor device

The invention claimed is:

1. A measurement method, comprising:
preparing a first reacting substance and a second reacting substance, the first reacting substance having a higher reactivity to a second detection target than to a first detection target, the second reacting substance having a higher reactivity to the first detection target than to the second detection target, wherein the first detection target comprises a first disease-associated proteinaceous substance and the second detection target comprises a second disease-associated proteinaceous substance;
preparing a sample;
making the sample contact with the first reacting substance and the second reacting substance;
measuring a first signal value of a first reaction between the first reacting substance and the sample, and a second signal value of a second reaction between the second reacting substance and the sample; and
calculating a relationship between the first detection target and the second detection target in the sample based on a calibration curve which is prepared in advance, the first signal value, and the second signal value, wherein the calibration curve is prepared in advance based on a first reference signal value and a second reference signal value, the first reference signal value being based on a reaction between the first reacting substance and at least one reference sample having known concentrations of the first and second detection targets, and the second reference signal value being based on a reaction between the second reacting substance and the at least one reference sample.

2. The measurement method according to claim 1, wherein the first reacting substance and the second reacting substance are each an antibody or an aptamer.

3. The measurement method according to claim 1, wherein the first reacting substance and the second reacting substance are each an RNA aptamer.

4. The measurement method according to claim 1, wherein
the first signal value and the second signal value are each a phase characteristic value.

5. The measurement method according to claim 1, wherein the first signal value and the second signal value are each a value measured using a method selected from among QCM, SPR, and FET.

6. The measurement method according to claim 1, wherein the sample is a blood sample.

7. The measurement method according to claim 1, wherein the first detection target and the second detection target are each a proteinaceous substance.

8. The measurement method according to claim 7, wherein the proteinaceous substance is a disease-associated proteinaceous substance.

* * * * *

SEQUENCE LISTING

<160> NUMBER OF SEQ ID NOS: 5

<210> SEQ ID NO 1
<211> LENGTH: 110
<212> TYPE: RNA

```
<213> ORGANISM: Artificial sequence
<220> FEATURE:
<223> OTHER INFORMATION: Synthetic RNA; RNA aptamer

<400> SEQUENCE: 1
gggauaggau ccacaucuac guauuacggc auuauuagga ccaaugcuga guacggcgca      60
cagcuuuuuu cacugcagac uugacgaagc uuaaaaaaaa aaaaaaaaaa                110

<210> SEQ ID NO 2
<211> LENGTH: 110
<212> TYPE: RNA
<213> ORGANISM: Artificial sequence
<220> FEATURE:
<223> OTHER INFORMATION: Synthetic RNA; RNA aptamer

<400> SEQUENCE: 2
gggauaggau ccacaucuac guauuagauu aggaccaaua cgugguuggc cccccucaa       60 cgacgcaguu cacugcagac uugacgaagc uuaaaaaaaa aaaaaaaaaa                110

<210> SEQ ID NO 3
<211> LENGTH: 18
<212> TYPE: DNA
<213> ORGANISM: Artificial Sequence
<220> FEATURE:
<223> OTHER INFORMATION: Synthetic DNA

<400> SEQUENCE: 3
tttttttttt tttttttt                                                    18

<210> SEQ ID NO 4
<211> LENGTH: 39
<212> TYPE: RNA
<213> ORGANISM: Artificial sequence
<220> FEATURE:
<223> OTHER INFORMATION: Synthetic RNA; RNA aptamer

<400> SEQUENCE: 4
ccacaucuac guauuagauu aggaccaaua cgugguugg                             39

<210> SEQ ID NO 5
<211> LENGTH: 36
<212> TYPE: RNA
<213> ORGANISM: Artificial sequence
<220> FEATURE:
<223> OTHER INFORMATION: Synthetic RNA; RNA aptamer

<400> SEQUENCE: 5
cguauuacgg cauuauuagg accaaugcug aguacg                                36
```